(12) United States Patent
Lipow

(10) Patent No.: US 7,198,630 B2
(45) Date of Patent: Apr. 3, 2007

(54) METHOD AND APPARATUS FOR CONTROLLING A SURGICAL ROBOT TO MIMIC, HARMONIZE AND ENHANCE THE NATURAL NEUROPHYSIOLOGICAL BEHAVIOR OF A SURGEON

(75) Inventor: Kenneth Lipow, Fairfield, CT (US)

(73) Assignee: Kenneth I. Lipow, Bridgeport, CT (US)

( * ) Notice: Subject to any disclaimer, the term of this patent is extended or adjusted under 35 U.S.C. 154(b) by 407 days.

(21) Appl. No.: 10/321,171

(22) Filed: Dec. 17, 2002

(65) Prior Publication Data
US 2004/0116906 A1 Jun. 17, 2004

(51) Int. Cl.
*A61B 19/00* (2006.01)

(52) U.S. Cl. .............................. 606/130; 414/1; 414/2; 606/1

(58) Field of Classification Search .................. 606/1, 606/13, 136, 130; 600/101, 141, 142, 144; 318/568.11; 901/2, 8, 9, 14, 27, 28; 414/1, 414/2
See application file for complete search history.

(56) References Cited

U.S. PATENT DOCUMENTS

| | | | |
|---|---|---|---|
| 5,762,458 A * | 6/1998 | Wang et al. ................ | 414/1 |
| 5,943,914 A | 8/1999 | Morimoto et al. | |
| 6,000,297 A * | 12/1999 | Morimoto et al. ........ | 74/479.01 |
| 6,104,158 A * | 8/2000 | Jacobus et al. ........ | 318/568.11 |
| 6,416,520 B1 | 7/2002 | Kynast et al. | |
| 6,463,319 B1 | 10/2002 | Bucholz | |
| 6,836,703 B2 * | 12/2004 | Wang et al. ................ | 700/258 |
| 2002/0082498 A1 | 6/2002 | Wendt et al. | |
| 2002/0122174 A1 | 9/2002 | Hamamatsu et al. | |

OTHER PUBLICATIONS

Web page http://www.globaltechnoscan.com/21stMar-27thMar01/robot.htm; "Robot-assisted brain surgery is feasible . . . ", Dec. 3, 2002.
Web page http://www.observer.co.uk/uk_news/story/0,6903,542571.html; "Brain surgery by robot gives hope to Parkinson's sufferers"; Dec. 3, 2002.
Web page http://www.time.com/time/health /article/0,8599,128361,00.html; "Forceps! Scalpel! Robot!"; Oct. 18, 2002.

(Continued)

*Primary Examiner*—Rosiland Rollins
(74) *Attorney, Agent, or Firm*—Reed Smith LLP

(57) ABSTRACT

The present invention was developed by a neurosurgeon and seeks to mimic the results of primate neurological research which is indicative of a human's actual neurological control structures and logic. Specifically, the motor proprioceptive and tactile neurophysiology functioning of the surgeon's hands and internal hand control system from the muscular level through the intrafusal fiber system of the neural network is considered in creating the robot and method of operation of the present invention. Therefore, the surgery is not slowed down as in the art, because the surgeon is in conscious and subsconscious natural agreement and harmonization with the robotically actuated surgical instruments based on neurological mimicing of the surgeon's behavior with the functioning of the robot. Therefore, the robot can enhance the surgeon's humanly limited senses while not introducing disruptive variables to the surgeon's naturally occurring operation of his neurophysiology. This is therefore also a new field, neurophysiological symbiotic robotics.

23 Claims, 7 Drawing Sheets

OTHER PUBLICATIONS

Web page Cardiothoracic Surgery at the Ohio State University of Nov. 18, 2002; "The DaVinci Robot"; Nov. 18, 2002.
Articles from: "Current Problems in Surgery," Matthew B. Bloom et al., vol. 39, No. 8, Aug. 2002, Mosby Corporate, pp. 736-739.
Article: "Robotic Surgery," D. Stoianovici, URobotics Laboratory, World Journal Urology (2000) 18: 289-295.
Article: "A review of robotics in surgery," B. Davies, Proc Instn Mech Engrs vol. 214 Part H, Oct. 22, 1999.
Web page: http://www.bmj.com/cgi/content/full "Robots in operating theatres" Nov. 12, 2000.
Article: "Is the Robotic Arm a Cost-effective Surgical Tool?" Karen Dunlap et al., Aorn Journal, Aug. 1998, vol. 68, No. 2.
Article: "Robots in the Operating Room," Kevin L. Ropp, FDA Consumer/Jul.-Aug. 1993/25.
Article: "Emerging Technologies for Surgery in the 21$^{st}$ Century," Richard M. Satava, Arch Surg/vol. 134, Nov. 1999.
Article: "A Teleoperated Microsurgical Robot and Associated Virtual Environment for Eye Surgery," Ian W. Hunter et al., Presence, vol. 2, No. 4, fall 1993, 265-280, The Massachusetts Institute of Technology.
Article: "Robotically Driven Interventions: A Method of Using CT Fluoroscopy without Radiation Exposure to the Physician," Stephen B. Solomon et al., RSNA, 2002.
Article: "Quantitative virtual reality enhances stereotactic neurosurgery," Patrick Kelly, vol. 80, No. 11, Bulletin of the American College of Surgeons, Nov. 1995.
Article:"NeuRobot: Telecontrolled Micromanipulator System for Minimally Invasive Microneurosurgery—Preliminary Results," Kazuhiro Hongo et al., Neurosurgery, vol. 51, No. 4, Oct. 2002, 985-988.
Article: "Robot for CT-Guided Stereotactic Neurosurgery," H. Fankhauser et al., Proceedings of the XIth Meeting of the World Society for Stereotactic and Functional Neurosurgery, Ixtapa, Mexico, Oct. 11-15, 1993.
Article: "Motion Feedback as a Navigation Aid in Robot Assisted Neurosurgery," Matthias Wapler et al., Medicine Meets Virtual Reality, IOS Press and Ohmsha, 1998.
Article: "Robotic Three-Dimensional Positioning of a Stimulation Electrode in the Brain," J-L. Hefti ET el., Computer Aided Surgery 3:1-10 (1998).
Article: "New Dimensions of Neurosurgery in the Realm of High Technology: Possibilities, Practicalities, Realities," Michael L. J. Apuzzo, Neurosurgery, vol. 38, No. 4, Apr. 1996.
Article: "A Robot with improved Absolute Positioning Accuracy for CT Guided Stereotactic Brain Surgery," Yik San Kwon, IEEE.
Article: "Application of robotics to stereotactic neurosurgery," Ronald F. Young, Neurosurgical Research, 1987, vol. 9, Jun.
Article: "ISG Viewing Wand System," Neurosurgery, vol. 34, No. 6, Jun. 1994.
Article: "The First Clinical Application of a Hands-On Robotic Knee Surgery System," M. Jakopec et al., Computer Aided Surgery, 6:329-339 (2001).
Article: "Machining and Accuracy Studies for a Tibial Knee Implant Using a Force-Controlled Robot," Geert Van Ham et al., Computer Aided Surgery, 3:123-133 (1998).
Article: "Anesthesia for Robotic Heart Surgery: An Overview," John M. Murkin, The Heart Surgery Forum #2001-7281, 4(4): 311-314, 2001.
Article: "Current Status and Future Directions in Computer-Enhanced Video- and Robotic-Assisted Coronary Bypass Surgery," W. Douglas Boyd et al., Seminars in Thoracic and Cardiovascular Surgery, vol. 14, No. 1 (Jan. 2002, pp. 101-109).
Article: "Robotic Stabilization that Assists Cardiac Surgery on Beating Hearts," Yoshihiko Nakamura et al., Medicine Meets Virtual Reality 2001.
The Internet Article: "A Robot that Fixes Hearts," Rob Younge et al., EBSCOhost Full Display, Source U.S. News and World Report, Dec. 25, 2000-Jan. 1, 2001, vol. 129, Issue 25, p. 50.
Article: "Comparison of Robotic Versus Human Laparoscopic Camera Control," Louis R. Kavoussi et al., The Journal of Urology, vol. 154, 2134-2136, Dec. 1995.
Article: "Feasibility of Robotic Laparoscopic Surgery: 146 Cases," Guy-Bernard Cadiere et al., World Journal of Surgery, 1467-1477, 2001.
Article: "Robot-Assisted Microsurgery: A Feasibility Study in the Rat," Peter D. Le Roux et al., Neurosurgery, vol. 48, No. 3, Mar. 2001.
Article: "Intraoperative Instrument Motion Sensing for Microsurgery," Mario Gomez-Blanco et al., Proceedings of the First Joint BMES/EMBS Conference Serving Humanity, Advancing Technology, Oct. 13-16, 1999, Atlanta, GA, USA.
Article: "An Active Hand-held Instrument for Enhanced Microsurgical Accuracy," Wei Tech Ang et al., Proceedings of the Third International Conference on Medical Image Computing and Computer-Assisted Intervention, Pittsburgh, PA, Oct. 11-14, 2000.
Article: "Neurosurgical Suite of the Future III," Garnette R. Sutherland et al., Neuroimaging Clinics of North America, vol. 11, No. 4, Nov. 2001.
Internet Article: "Robotic surgery, telerobotic surgery, telepresence, and telementoring", G.H. Ballantyne, http://link.springer.de/link/service/journals/00464/contents/01/8283/paper/body.html, 2002.
Article: "A Force-Reflecting Teleoperated Hand System for the Study of Tactile Sensing in Precision Manipulation", Robert D. Howe, Proceedings of the 1992 IEEE International Conference on Robotics and Automation, Nice, France, May 1992.
Article: "Computer-Guided Microsurgery: Surgical Evaluation of a Telerobotic Arm", B. D. Krapohl, et al., Microsurgery, 21:22-29, 2001.
Article: Rajesh Kumar et al.; "Performance of Robotic Augmentation in Microsurgery-Scale Motions"; John Hopkins University (undated).
Article: Rajesh Kumar et al.; Proceedings of the 2000 IEEE International Conference on Robotics and Automation; "Preliminary Experiments in Cooperative Human/Robot Force Control for Robot Assisted Microsurgical Manipulation".
Article: Andrew Bzostek et al.; Submitted for Consideration to MICCAI'99; "Force vs. Deforamtion in soft tissue puncture".
Internet Article: http://www.mein.nagoya-u.ac.ip/activity/introduction.html; Cellular Robotic System (CEBOT); Dec. 3, 2002.
Article: Ales Bardorfer et al, Melecon 2000—10$^{th}$ Mediterranean Electrotechnical Conference May 29-31, 2000 Cyprus; "Connecting Haptic Interface with a Robot".
Article: Russell Taylor et al.; International Journal Of Robotics Research, 18 (12): 1201-1210 Dec. 1999; "A Steady-Hand Robotic System for Microsurgical Augmentation".
Article: Minyan Shi et al.; Virginia Neurological Institute, Jun. 17, 1997; "Integrated Remote Neurosurgery System".
Web page: http://www.neurosurgery-online.com/abstracts/4803/NURO48030584_abstx.html; Peter D. Le Roux et al.; Robot-assisted Microsurgery: A Feasibility Study in the Rat; Dec. 3, 2002.
Web page: http://www.sensable.com/haptics/haptics.html; Haptics Research; Dec. 3, 2002.
Web page http://www.robotbooks.com/robot-surgeon.htm; "Robots in the News"; Dec. 3, 2002.

* cited by examiner

METHOD AND APPARATUS FOR CONTROLLING A SURGICAL ROBOT TO MIMIC, HARMONIZE AND ENHANCE THE NATURAL NEUROPHYSIOLOGICAL BEHAVIOR OF A SURGEON

BACKGROUND

The present invention relates to the field of robotic and computer assisted surgery. It may also be used for many different types of microsurgery. For example, neurosurgery, spine, ear nose and throat surgery, microplastic surgery, and eye surgery.

As shown in U.S. Pat. No. 5,943,914 to Morimoto et al., "Master/slave" robots are known in which a surgeon's hand input is converted to a robotic movement. This is particularly useful for motion scaling wherein a larger motion in millimeters or centimeters by the surgeon's input is scaled into a smaller micron movement. Motion scaling has also been applied in cardiac endoscopy, and neurosurgical target acquisition brain biopsy (with a needle) but only in one degree of freedom, for example only for insertion, not for a full range of natural hand movement directions, .e., not for all possible degrees of natural motion, Cartesian, spherical or polar coordinate systems or other coordinate systems.

Further, in the prior art, surgical robots have been purposefully designed to eliminate the natural hand tremor motions of a surgeon's hand which is about a 50 micron tremor which oscillates with some regularity. The common presumption is that tremor motion creates inaccuracies in surgery. Therefore, robots have been tested which entirely eliminate the surgeon's natural hand tremor. See "A Steady-Hand Robotic System for Microsurgical Augmentation" Taylor et al., *International Journal Of Robotics Research,* 18(12):1201–1210 December 199, and also see "Robotic-assisted Microsurgery: A Feasibility Study in the Rat" LeRoux etal., *Neurosurgery*, March 2001, Volume 48, Number 3, page 584.

Force reflectance sensing is also known in order to provide tactile or haptic feedback to a surgeon via an interface. See "Connecting Haptic Interface with a Robot" Bardofer et al., Melecon 200—10$^{th}$ Mediterranean Electrotechnical Conference, May 29–31 2000, Cyprus.

However, in testing, all of these techniques ultimately slow down the actual surgery especially when performed in conjunction with a microscope for viewing the operation. The procedure time is typically increased by two to three times. See Robotic-assisted Microsurgery: A Feasibility Study in the Rat" cited above.

Additionally, there is a major design issue regarding the choice between locating the surgeon in his normal operating position about the patient's head or locating the surgeon more remotely from the normal operating position at a terminal with a joystick and viewing screen for example. The prior art elects to locate the surgeon remotely from the traditional operational position about the head and to use monitors to display the operation to the surgeon.

SUMMARY OF THE INVENTION

The present invention was developed by a neurosurgeon and seeks to mimic the results of primate neurological research which is indicative of a human's actual neurological control structures and logic. Specifically, the proprioceptive and tactile neurophysiology functioning of the surgeon's hands and internal hand control system from the muscular level through the intrafusal fiber system of the neural network is considered in creating the robot and method of operation of the present invention Therefore, the surgery is not slowed down as in the art, because the surgeon is in conscious and subsconscious natural agreement and harmonization with the robotically actuated surgical instruments based on neurological mimicing of the surgeon's behavior with the functioning of the robot. Therefore, the robot can enhance the surgeon's humanly limited senses while not introducing disruptive variables to the surgeon's naturally occurring operation of his neurophysiology. This is therefore also a new field, neurophysiological symbiotic robotics.

One result of the present invention, and associated discoveries, was that preservation of the hand tremor motion was unexpectedly found to be necessary, to an extent, to maintain a natural and efficient synergy between the human surgeon and the robotics in order to maintain the normal pace of surgery. This is because the present invention inventively recognizes that the surgeon's own neurophysiology beneficially uses tremor motion, and moreover the human body expects and anticipates the tremor to exist for calibration purposes. For example, at the muscular level, tremor is used neurologically for automated feedback sensory scaling and also as part of probing, positioning, and training process of the muscle spindle and muscle. Therefore, human muscle actually performs some calibration and "thinking" itself including anticipating forces to come based on historically learned data or instinct. Thus, preservation of hand tremor is counter-intuitive, and the opposite of what is taught and suggested in the art.

The present invention locates the controller robot to work in basically the same orientation and location as in a standard manual operation. In neurosurgery for example, the controller robot may be included in a halo structure fixed to the patient's head in much the same way as a standard retractor system is affixed. Alternatively, the controller robot may be located on a stand, the body, on the O.R. table or on a rolling or portable platform. In this manner, the surgeon is not immediately forced to operate in an unnatural, detached and isolated environment which is foreign to traditional procedures to which his own body and neurological responses are accustomed. This is the opposite of the teachings of the art which favor a more remotely located and integrated display and/or joystick arrangement.

Therefore, in summary, the present invention in its various controller robot embodiments includes the following features which are adjustable by the surgeon to his individual requirements:

Hand tremor sensing, management, modulation and smoothing with scaling capability in all natural and anatomical degrees of freedom directions;

Motion sensing and scaling in all natural and anatomical degrees of freedom directions;

Force sensing and scaling including squeeze force scaling, and force reflectance feedback scaling in all natural and anatomical degrees of freedom directions;

Contact sensing and indicating contact, including in a binary manner, all natural and anatomical degrees of freedom directions;

Contact reflectance sensing, i.e., reflectance force on the tip of the instrument all natural and anatomical degrees of freedom directions;

Mini endoscopic "tip vision" sensors located to look down the tip of the surgical instrument;

Magnetic MRI navigation interface capabilities;

Microscope interface capabilities;

Tool selector interface capability to automatically change surgical tools;

DETAILED DESCRIPTION OF THE INVENTION, PREFERRED EMBODIMENT, AND BEST MODE

Figure 4:
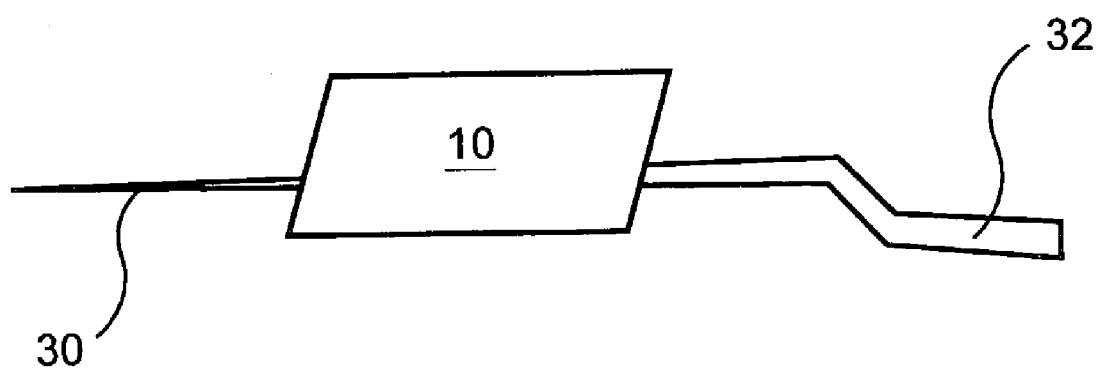
FIG. 4 shows conceptually the present invention.
Figure 5A:
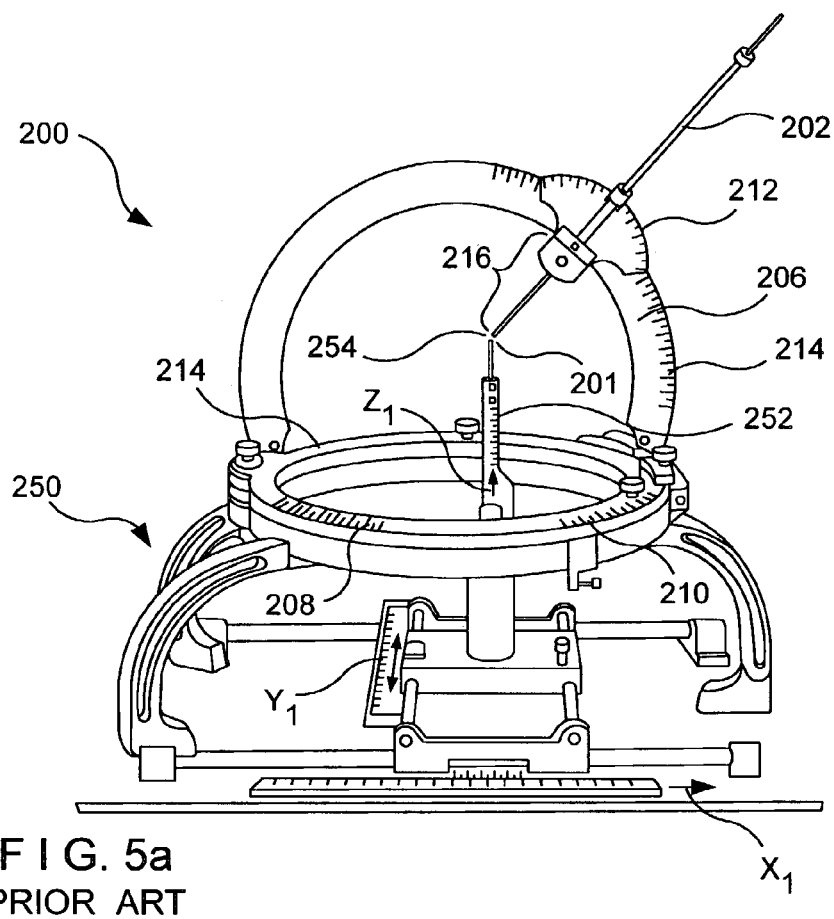
FIG. 5 shows a prior art mount for surgery from U.S. Pat. No. 6,463,319.
Figure 5B:
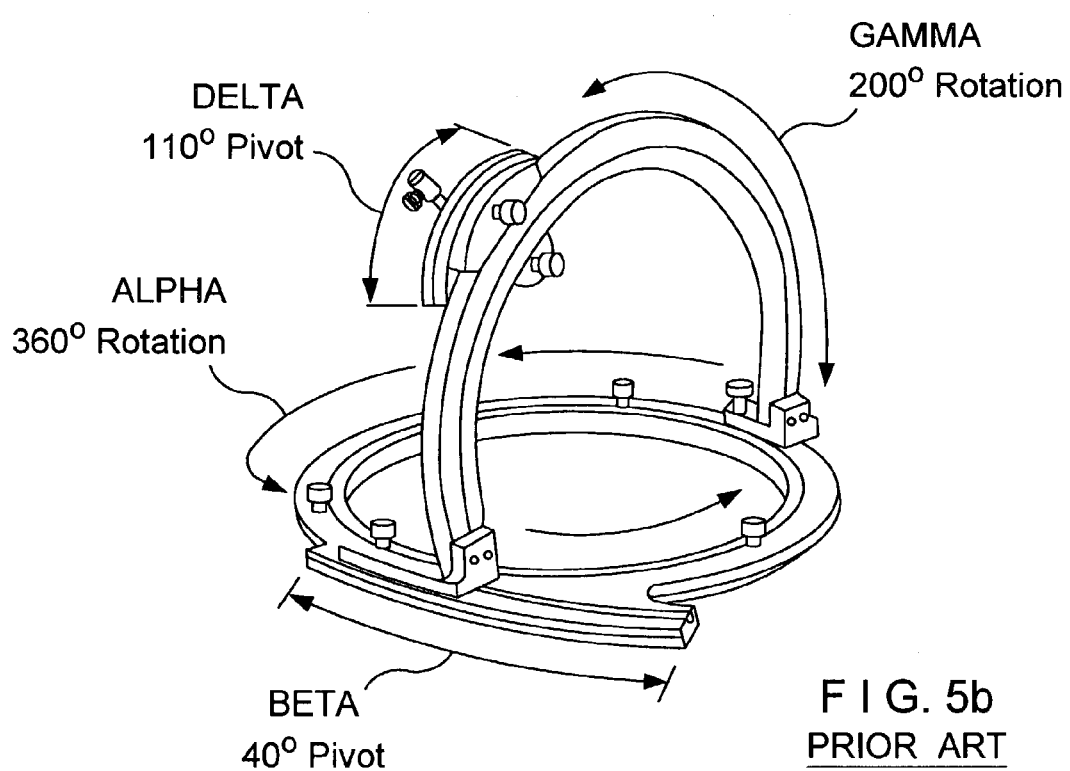

FIG. 4 shows conceptually how the present invention directly creates a virtual surgical instrument by placing controller robot 10 between the surgical instrument 30 and the handle 32 of the instrument. In this way, the surgeon is not isolated or made remote from the operation, but instead maintains the environment to which he is accustomed.

Extrapolating new surgical concepts from known primate research have been critical to method of the present invention, as described generally below.

The way the primate body handles proprioceptive perception is via sensory feedback scaling (up and down) at the muscular level through the intrafusal fiber system of the Gamma efferent neural circuit. This system responds dynamically to changes in the anticipated muscle performance requirement at any instance by adjusting muscle tone with increased discharging for arousal and attention focusing states, and decrease output for resting and low attention states. The muscle spindle apparatus that does this is located in the muscle body, therefore feedback sensory scaling for muscle positioning, force, length and acceleration is partly programmed at the effector level in "hardware" of the body, i.e., the muscle itself. The evidence indicates a 10 cycle per second refresh rate for the human neurophysiological system in general.

Joint position and fine motor function of the fingers occurs through unidirectional (50% of fibers) and bi-directional (50% of fibers) sensing at the joint structure. This coding is for rotation about an axis, but not for force and no clear speed of rotation feedback.

Cutaneous receptors in the skin code for motion, by modulating higher centers in the thalamus and cerebral cortex. This can be timed to about 75 ms delays before motion occurs, three neuronal synaptic transmission delays. These sensors are primarily distal to the joint of rotation and distal in the moving effector limb. Finally, the sense of contact is totally discrete from the above motion feedback sensory systems and the neural pathways and integration centers in the deep hemispheres and cerebral cortices function independent of motion to a large degree.

Figure 1:
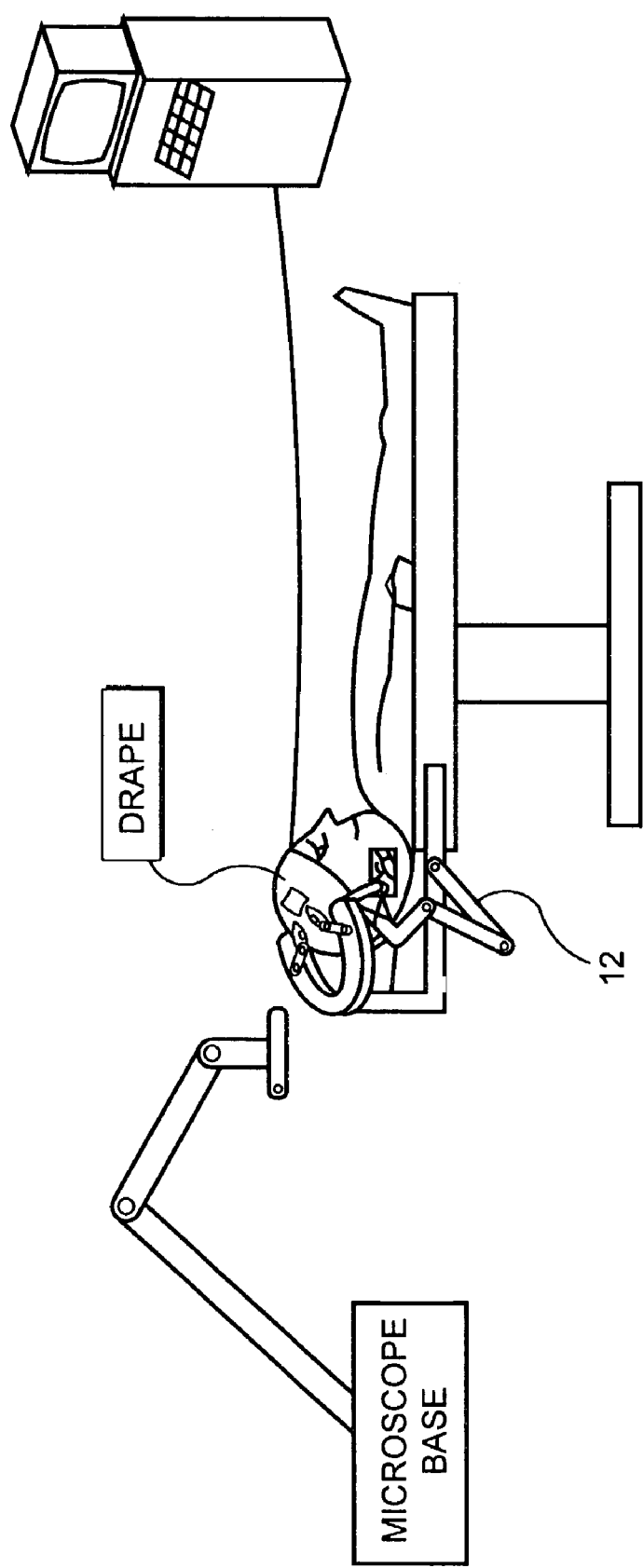
FIG. 1 is a side view of the a patient on an operating table with the controller robot in place on the patient.
Figure 2:
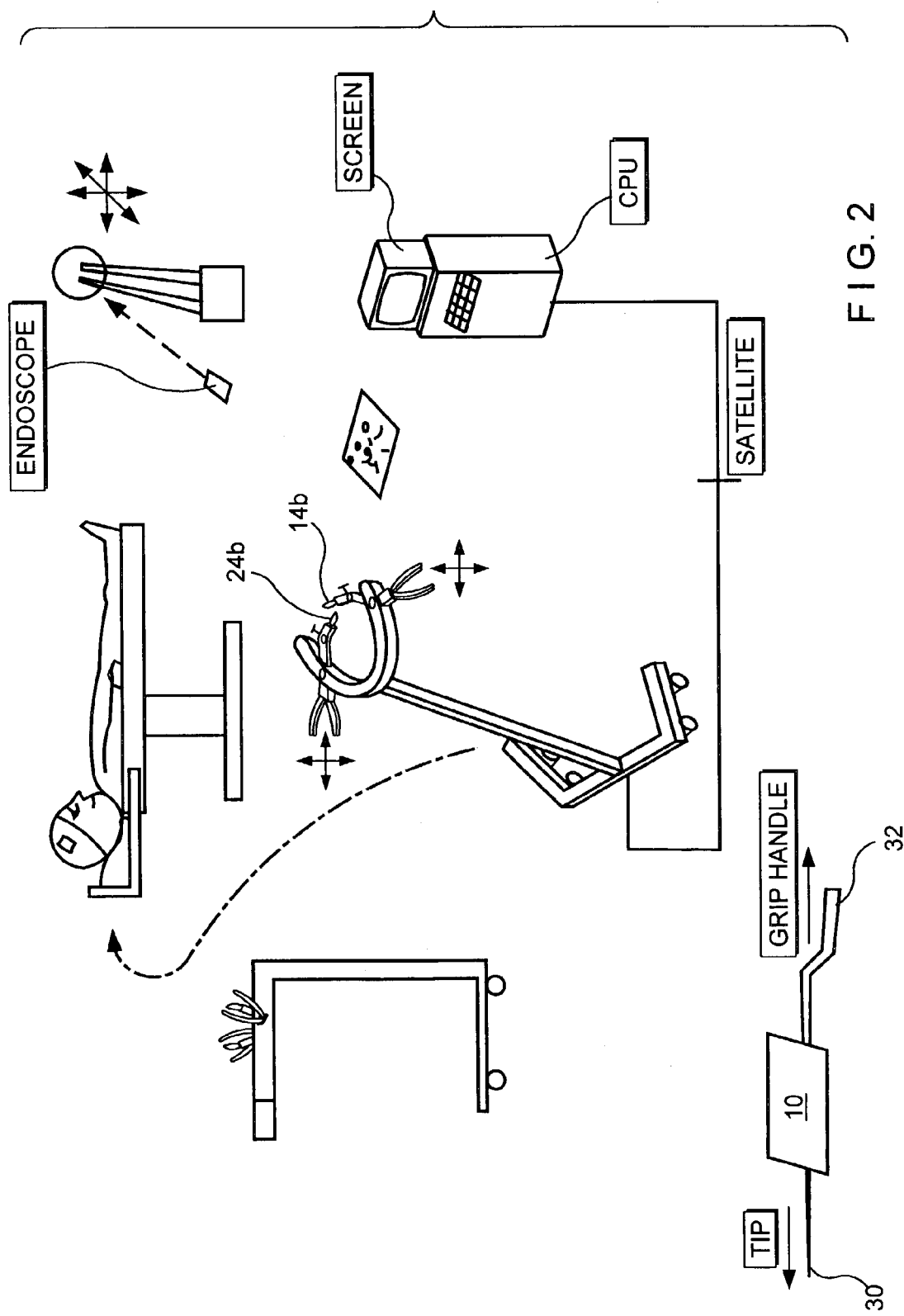
FIG. 2 is top view of a second embodiment of the controller robot in which the controller robot is affixed to a stand.
Figure 3:
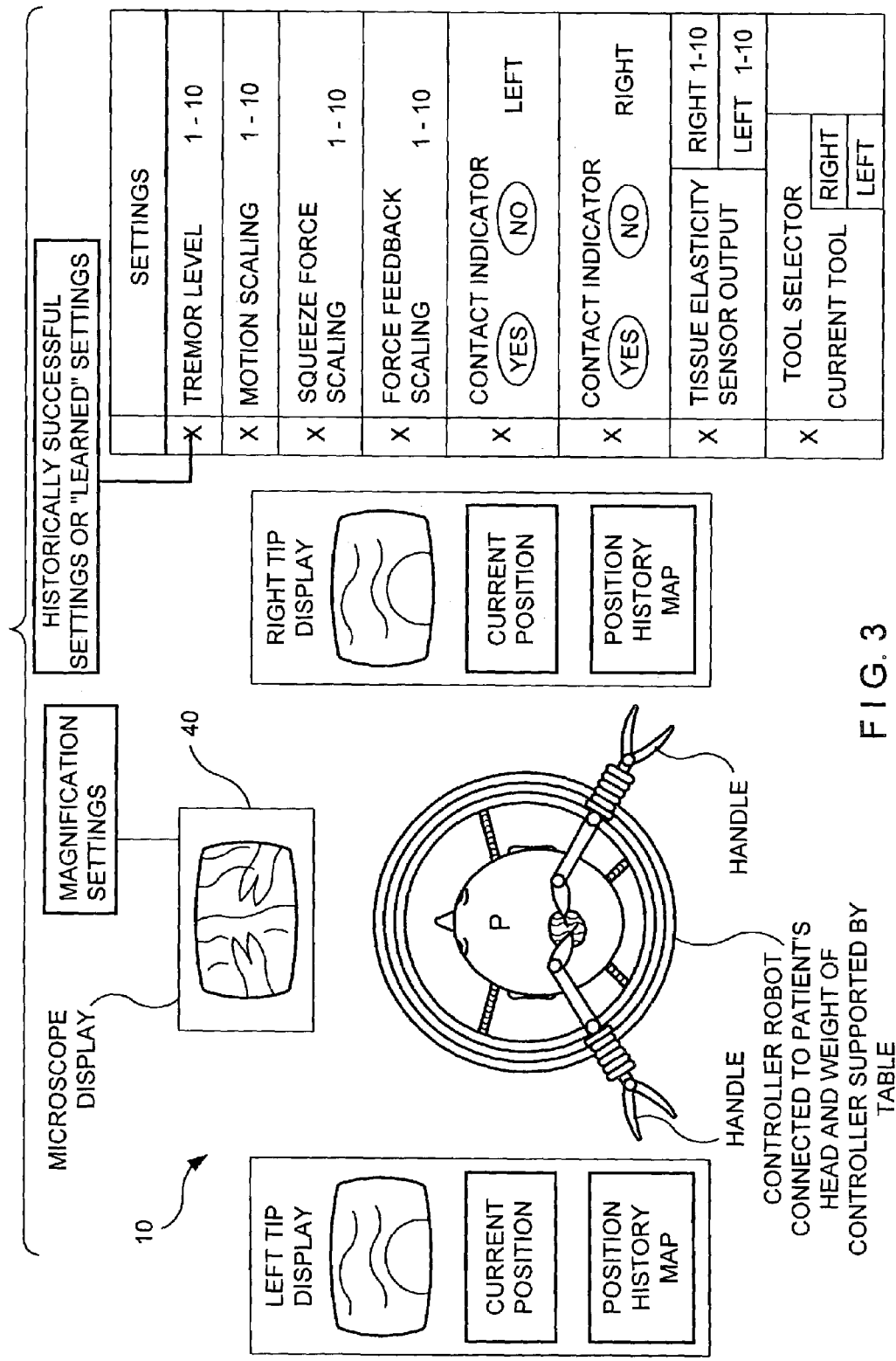
FIG. 3 is a representation of the controller robot in operation with its accompanying data displays to the surgeon represented.

Therefore, as shown in FIGS. 1–3, in the controller robot 10 of the present invention, the creation of the perception of "contact" per se in a surgical robot controller robot 10 should not be based on acceleration/motion reflectance to properly mimic the human neurological system but rather should be based purely on a binary sense of touch (see "contact indicator" display in FIG. 3); which is different from motion sense.

In a human, the motion sense takes over after the contact information has been initiated with fairly fixed delays measured in milliseconds. In the present invention, this can be transferred through the controller robot 10 to the handle 32 to the surgeon's hand as a mechanical physical impression such as a jerk or vibration, or optically or sonically through a display verifying the contact with the target or proximate tissue in the surgical field.

True force reflectance perception has to have high refresh rates measured in milliseconds. This is consistent with numbers described in the prior art literature which give tactile bandwidths on the order of 500–1000 Hz. For tool contact with soft surfaces, 100–200 Hz may be more than adequate.

The information the muscle sense is seeking to allow the operator to synthesize virtually in the controller robot, is amplitude and time with suitable rise and fall curves for the discrete motor performance function in question.

Also, the present invention inventively integrates the concept that the entire human sensory/motor neurophysiologic system works in an "anticipatory mode" with modulation by internal experience and external sensory data indicated above. This defines the need for suitable anticipatory delays between contact, muscle loading and neural transmissions times. All of these parameters will be scrutinized subconsciously by the operator via the optical feedback (microscope direct vision or endoscopic instrument tip tracking), during the surgery.

Figure 1A:
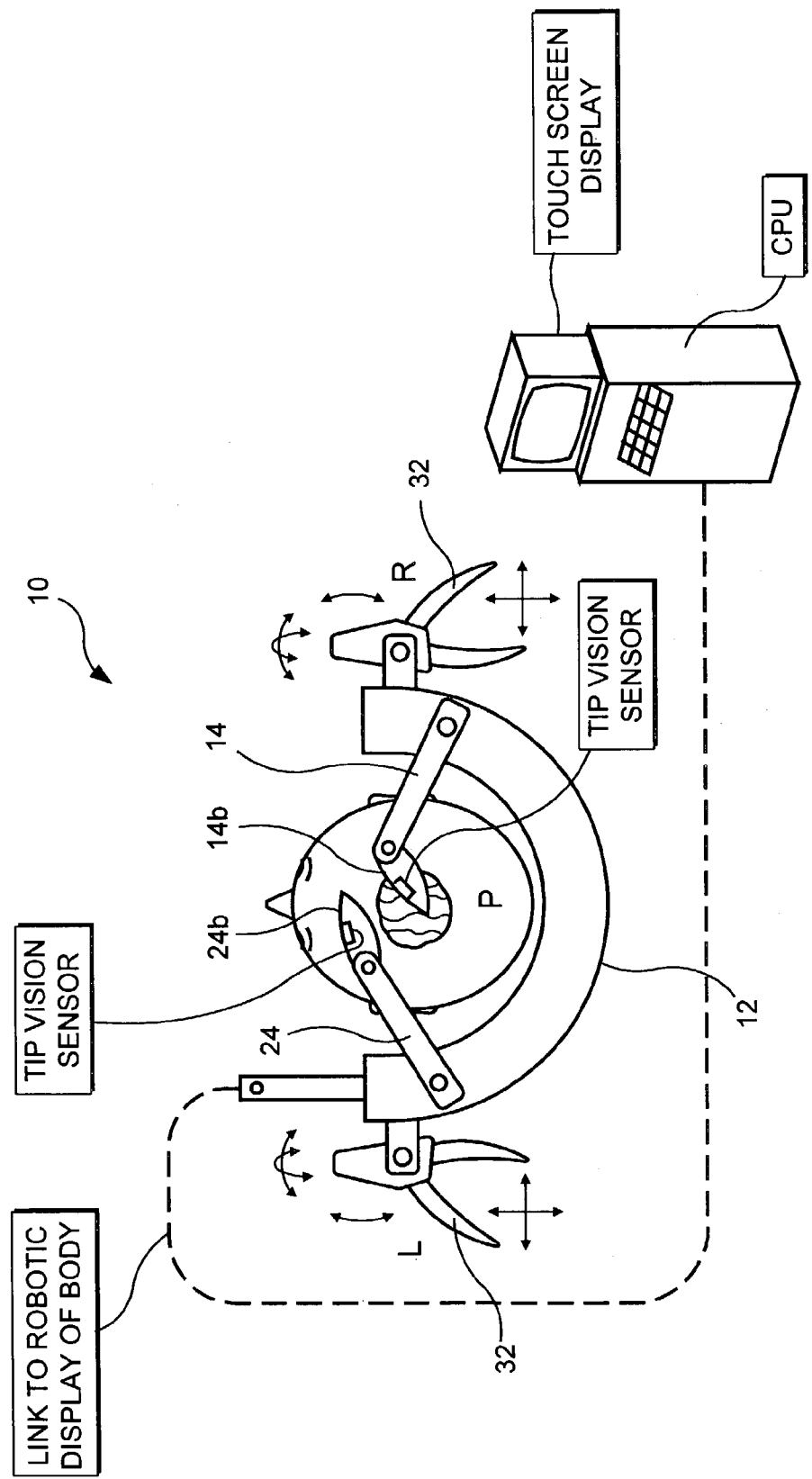
FIG. 1a is a top view of the controller robot in place on a patient.
Figure 1B:
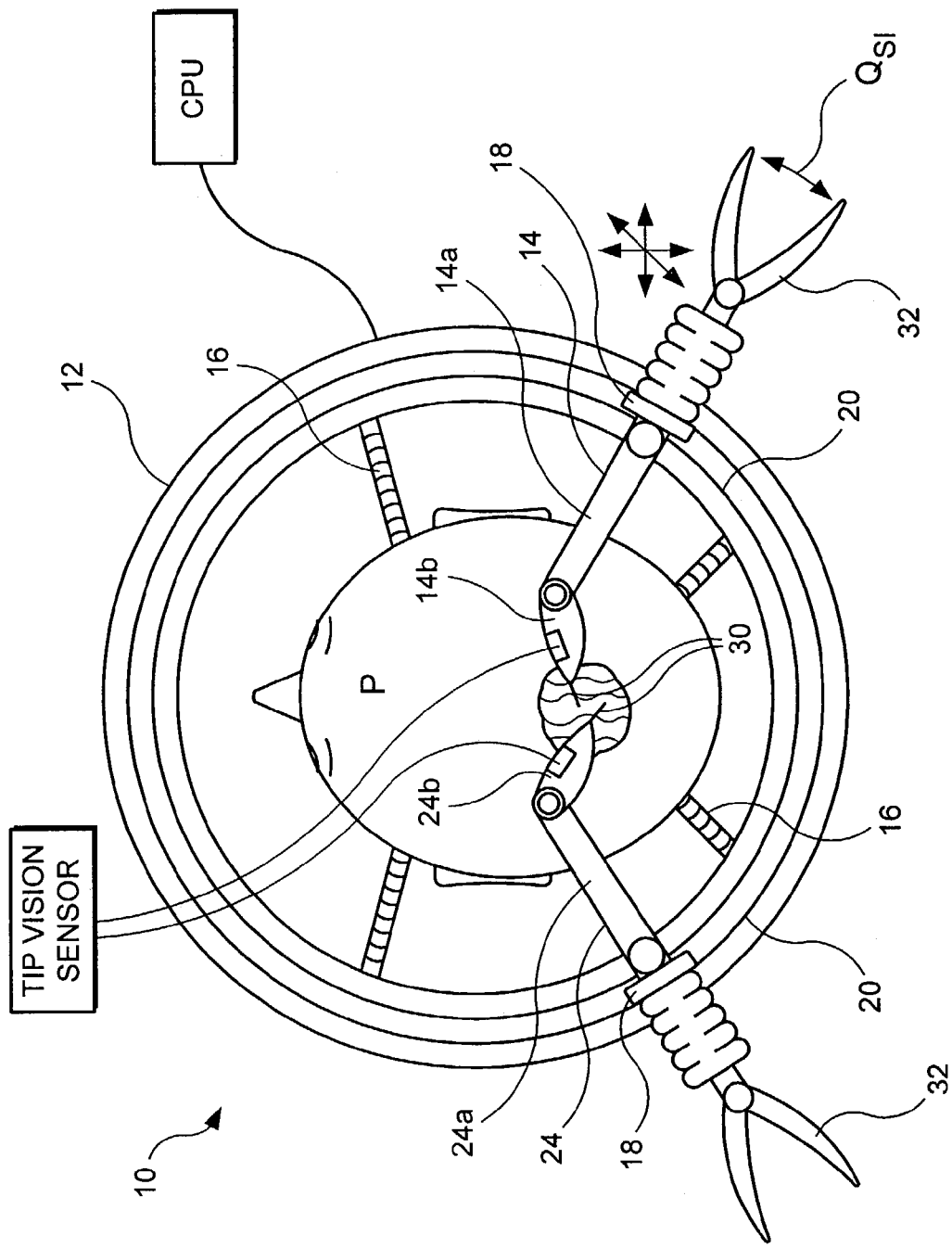
FIG. 1b is a top view of the controller robot in place on a patient.

In light of the above, the preferred embodiment and best mode for a neurological robot is discussed below. FIGS. 1a and 1b show the parts of controller robot 10 located about the head during surgery. A pinned head holder 12 is attached via cranial screws 16 the patient P. The pinned head holder 12 provides a base for mounting right robotic arm 14 and left robotic 24 via robotic arm mounts 18. Robotic arm mounts 18 are shown as motorized and provide for controlled motion including motion on the micron scale or smaller, and are moveable and stabilized in radial tracks 20. The robotic arms may include sub-arms such as those shown in 14a, 14b, 24a, and 24b. Alternatively, the robot arm may be mounted on a portable tray system which would be fixed to the table which is turn fixed to the patient or other combination for fixation. Surgical instruments are located at the end of the robotic arms as shown and may be interchanged as in any end effector apparatus. An automatic tool changer such as a carousel is contemplated as well. Handles 32 mimic actual handles from manual surgical instruments. i.e., they are the same size and shape, and can be squeezeable or fixed, in order to provide realism to the surgeon.

FIG. 3 shows a number of the data displays which are envisioned as part of controller robot 10.

Typically, a microscope display 40 is used to view a neurosurgery site on for example a microsurgery scale where surgical movements of the surgical instrument tips can be on the order of 100 micrometers. When viewing the operation through the microscope the surgeon is viewing a magnified image so his own movements are magnified. Therefore, motion scaling wherein a controller robot scales down the surgeon's movement of for example to 1 cm to 100 micrometers is obviously very useful. However, in the art, motion scaling in all natural anatomical hand motion degrees of freedom has not been taught or suggested as in the present invention.

Therefore, a settings display 50, which includes a motion scaling device is included as part of controller robot 10. The display includes hardware which runs software to control the motorized robotic arms. The display may be a touch screen or other interface, however the software, and hardware may be of any suitable design and this invention is not limited to any particular hardware, software or robotics per se. The present invention prefers to use robust hardware and software platforms for control electronics as required for space based applications where failure prevention is paramount, see applicable ISO and/or IEEE standards. Each surgeon who uses the robot controller 10 can store his personal settings so that his customized settings can be reproduced and the machine will not have to be retrained.

Returning to FIG. 3, the other adjustable settings are shown. A novel, counter-intuitive, and unexpected result of the present invention in concept and in reduction to practice is the significance of tremor regulation and management including both scaling and smoothing of the tremor oscillation. Hand tremor is one of the spurious motions present in surgery. Neurological tremor is usually a 50 micrometer (or micron) range excursion and is an oscillation with some regularity that increases with stress. A trained neurosurgeon's hand tremor is usually in the range of 50 to 100 microns, i.e., under a millimeter. The present invention significantly realizes and implements the fact that primate research suggests that hand tremor is not an unwanted artifact of evolution, instead it is a useful and necessary product of human evolution used for natural calibration. Typically, a hand tremor frequency can be at about 8 cycles per second and this regularity is used by the surgeon's nervous system to calibrate his movements. This neurological operational fact is recognized and utilized by the present invention, i.e., the human nervous system uses tremor to calibrate its movements almost automatically or subconsciously, and particularly in conjunction with coordination with optical recognition, i.e., hand/eye, when a surgeon moves his hands his eyes register and acknowledge the tremor which is used to calibrate his movements neurologically. This neurological fact is ignored by systems which seek to entirely filter and eliminate neurological tremor. This logic transfers to the tip of the surgical instrument, i.e., a surgeon looking through a microscope at the tip of his hand held instrument will see tremor motion and his own neurological system within his body will use tremor to neurologically and automatically calibrate his eye motions with his hand motion. Therefore, the present invention discloses and claims the new concept that tremor management is very important to surgeons and to any human mimicking robotics. This is the opposite of the prior art teachings.

In practice, due to magnification under a microscope during microsurgery such as neurosurgery, the surgeon's own optical system is not in 1:1 natural correspondence with the optical image. Therefore, "tremor scaling," i.e., modulating and adjusting the force of the tremor outputted to the surgical instrument to be harmonized at a natural level with the optical magnification selected, is also a very important concept of the present invention which is provided via the controller robot 10. This tremor scaling also helps to not impede the pace of the operation as in surgery. The tremor scaling feature is preferably also implemented in conjunction and harmony with motion scaling. For example, reducing natural tremor to half speed may improve the surgeon's movement. This is because the controller robot 10 in toto has enhanced the surgeon's movements.

For example, a typical surgeon's real hand motion or excursion of 5 centimeters with the surgical instrument contains a 50 micron tremor excursion oscillation, and the motion at the surgical instrument tip (at the actual surgical site) is scaled down by the controller robot 10 to become a 5 millimeter motion (motion scaling) but also includes a scaled down tremor motion of 2 microns (or any value the surgeon is personally comfortable with given settings based on trial and error and saving the best settings in the controller robot 10 from one surgery to the next). Thus, the controller robot has effectively maintained, in a relative fashion, the natural feeling of the surgeon's hand excursion even under magnification under the surgical microscope, i.e., through scaling. Therefore, when the surgeon looks at the surgical instrument through the microscope what he sees is a robotically controlled but natural looking 2 micron tremor excursion (minified from 50 microns) over his 5 millimeter motion (minified from 5 centimeters). This enhances the surgeon's actual useable natural range and allows him to have enhanced capabilities by first allowing him make his hand motions on a human scale of 5 centimeters and then scaling his motion down to 5 millimeters. Therefore, he does not have to try to move his hand accurately in the micron range. This scaling is performed by the present invention controller robot 10 in all degrees of freedom, i.e. any motion or directional path the human hand can make with a surgical instrument during a manual operation, the controller robot can make. Second, by incorporating and scaling a tremor motion the natural calibration of his neurological system is maintained when he looks through the microscope.

Additionally, given that calibration based on tremor is an important feature for proper motion of the surgeon's hand, the present invention also teaches that eliminating or processing anomalies from the tremor oscillation and resulting calibration, can help the neurological system to better self-calibrate itself. This is a inventive process that the present invention terms "tremor smoothing" or "tremor shaping." Therefore, if a surgeon is looking at the tip of an instrument his optical response which controls his hand can be aided and sped up if anomalies and great irregular deviations in his tremor signal are smoothed to be an oscillation with cyclical regularity. Thus, "tremor smoothing" can actually speed up the natural neurological calibration, rather than slowing it down by eliminating tremor as taught in the prior art.

It is envisioned that in the present invention the controller robot 10 when first used will have to be trained, i.e., optimal settings determined on animal tissue, in order for the surgeon's initial settings to be set up. Thereafter, the surgeon, while actually using the controller robot 10 on humans, will also store his settings which can be analyzed in real time. Therefore, the surgeon can have many modes and "can shift gears" depending on his preferred settings which are personalized to his requirements. Therefore, enabling personalized surgical robotic symbiosis is another new feature of the present invention which gives the controller robot a layer of artificial intelligence which is designed to mimic the artificial intelligence or natural responses naturally present in the neurological system and for example in the muscle tissue.

Force scaling is accomplished by the present invention in all degrees of anatomical motion. For example, a neurosurgeon may only be only humanly capable of inputting 0.01 Newtons of force as his minimum force to be applied to a surgical instrument. However, delicate tissue requires a much smaller force to be applied without damage. Therefore, force scaling allows any surgeon to enhance and minify the actual force presented to the surgical instrument 30. This is accomplished though the controller robot 10. Significantly, this enhances the surgeon's natural perception of the tissue's resistance, density, and elasticity.

The present invention enables force scaling in all anatomically natural hand movement directions, i.e., the scaling is not limited to one direction as in some prior art cardiac endoscopy robots for example. Therefore, all degrees of freedom of movement are enabled. For example, the controller robot can move the surgical instrument in eight degrees of freedom in one embodiment.

Force feedback or force reflectance enables the tip of the surgical instrument to relay to the controller robot 10, the feedback forces (which it actually senses via a sensor) to the handle 32. This enablement of feedback on the handle 32 becomes a virtual reality representation of the microsurgery environment and the tip. This force feedback is also capable of being scaled in a continuous real time fashion. Continuous resistance, elasticity, kickback movements, jerks or other movements can be presented at the handle 32 as they occur at the surgical instrument 30 tip. Significantly, some of these forces are so small that they need to be scaled up in level to be felt by the surgeon. Therefore, force reflectance enables the surgeon to actual feel feedback via the handle which he is not naturally capable of feeling. Therefore, it enhances his senses.

Contact sensing is also enabled by the present invention. Contact is a binary logic circuit in human neurology, i.e., either there is contact with tissue or not. It is not a time varying function of force as in force reflectance above. Therefore, the present invention harmonizes the body's natural "binary" contact sensing circuit by implementing a binary contact sensor and display (see FIG. 3, Contact "Yes," "No"). A scaled jerk motion can presented to the handle 32 to represent contact. This scaling enables the surgeon to feel small contacts (i.e., delicate tissue) which he would not be naturally able to feel.

Mini-endoscopic tip-vision capability is also taught and suggested by the present invention to enable a view down the tip of the instrument. This tip display enables vision from angles which are impossible to see through the traditional microscope view finder of the known surgical microscopes. The displays for the endoscopes are shown as right endoscopic tip display 60 and left endoscopic tip display 70 in FIG. 3. The displays are capable of showing many views, magnifications, current position, and history display of the course the instrument has traveled during the operation. Playback of actual images, "instant re-play of the operation moves" is also part of the history capability.

It is also contemplated that the handle 32 may be interchangeable and exchangeable to mimic actual standard surgical handles depending on field specific, surgeon specific, and operation specific conditions. For example, some handles may be squeezable, while some may be different shapes.

Other variations and modifications of the present invention will be apparent to those of skill in the art, and it is the intent of the appended claims that such variations and modifications be covered. The particular values and configurations discussed above can be varied and are cited merely to illustrate a particular embodiment of the present invention and are not intended to limit the scope of the invention. It is contemplated that the use of the present invention can involve components having different characteristics as long as the principles of the invention are followed.

What is claimed is:

1. A method of controlling a surgical instrument connected to a surgical robot for a surgeon comprising the steps of:
   locating a controller robot between a handle and a surgical instrument;
   sensing incident tremor force components present generated by the surgeon's hand on the handle;
   modulating the incident tremor force components in the controller robot; and
   outputting through the controller robot a modulated tremor force on the surgical instrument.

2. The method of claim 1 further comprising the step of:
   displaying a signal representing the modulated tremor force on a display.

3. The method of claim 2 further comprising the step of:
   controlling and adjusting the modulated tremor force to the surgeon's settings via an input.

4. The method of claim 1 further comprising the step of:
   attaching the controller robot to a patient's head via cranial screws.

5. The method of claim 1 wherein the modulation of the incident tremor force is outputted in all anatomically possible movement directions of the human hand.

6. The method of claim 5 wherein the modulation of the incident tremor force is determined by the surgeon's instructions and supplemented in the controller robot with historical data specific to the surgeon.

7. The method of claim 1 wherein at the step of outputting through the controller robot a modulated tremor force on the surgical instrument;
   the output is scaled and/or smoothed.

8. The method of claim 1 wherein at the step of outputting through the controller robot a modulated tremor force on the surgical instrument;
   the output is smoothed to eliminate anomalies.

9. The method of claim 8 wherein the smoothing comprises modulating a frequency signal derived from the incident tremor force components in the controller robot.

10. The method of claim 9 wherein the smoothing improves a natural neurological calibration of the surgeon's hand/eye coordination neural circuits and brain function.

11. A method of controlling a surgical instrument connected to a surgical robot comprising the steps of:
    locating a controller robot between a handle and a surgical instrument;
    sensing incident reflectance force from a sensor when the surgical instrument is placed against body tissue;
    modulating the reflectance force components in the controller robot;
    and outputting through the controller robot a modulated reflectance force on the handle.

12. The method of claim 11 comprising the further step of:
    computing the tissue elasticity coefficient in the controller robot from the sensed reflectance force.

13. The method of claim 11 comprising the further step of:
    scaling the sensed reflectance force to a scaled output level for outputting through the controller robot.

14. The method of claim 13 wherein during the scaling step, naturally human unsensable reflectance forces are scaled upwards by the controller robot to enable human level sensing on the handle.

15. The method of claim 11 wherein the modulation scaling step includes the further step of outputting in all anatomically possible movement directions of the human hand.

16. The method of claim 11 wherein the output is outputted in all anatomically possible movement directions of the human hand.

17. A method of controlling by a surgeon a surgical instrument connected to a surgical robot comprising the steps of:
locating a controller robot between a handle and a surgical instrument;
sensing incident tremor force components (TF) present on the handle generated by the surgeon's hand;
sensing an incident motion force (MF) component present on the handle generated by the surgeon's hand natural motion (NM) as the surgeon moves the handle;
modulating and scaling the incident tremor force (MTF) components in the controller robot;
modulating and scaling the incident motion force (MMF) components in the controller robot;
creating a modulated and scaled output movement (MSOM) including the modulated and scaled incident motion force (MMF) and the modulated and scaled incident tremor force (MTF) in the controller robot for moving the surgical instrument via the controller robot, with all anatomically possible degrees of human hand motion freedom, in response to the natural movement (NM) inputted by the surgeon on the handle;
outputting the modulated and scaled movement (MSOM) to move the surgical instrument with all anatomically possible degrees of human hand motion freedom, in response to a respective natural movement (NM) inputted by the surgeon on the handle;
sensing incident reflectance force (RF) components from the surgical instrument in the controller robot when the surgical instrument is near body tissue;
modulating and scaling the reflectance force (RFMS) components in the controller robot;
outputting at the handle the modulated and scaled reflectance force (RFMS);
sensing contact in a binary manner with the tissue (TC) in the controller robot;
sending a contact signal to a display and creating in the controller robot a scaled jerk motion in the handle to represent contact to the surgeon.

18. The method of claim 17 further comprising the steps of:
viewing the tip of the surgical instrument by locating a mini-endoscope on the robot controller to gather an image; and
displaying the image on a display including instant replay capability.

19. The method of claim 17 further comprising the step of:
viewing the surgical instruments through a microscope viewer.

20. The method of claim 17 wherein at the step of modulating and scaling the incident tremor force (MTF) components in the controller robot;
the modulation included a smoothing of the incident tremor force (TF) to remove anomalies in the modulated and scaled incident tremor force (MTF).

21. A surgical robot for a surgeon comprising:
a controller robot located between a handle and a surgical instrument;
a sensor for sensing incident tremor force components present generated by the surgeon's hand on the handle;
a modulator for modulating the incident tremor force components in the controller robot; and
a motor for outputting through the controller robot a modulated tremor force on the surgical instrument.

22. A surgical robot comprising:
a controller robot located between a handle and a surgical instrument;
a sensor for sensing an incident reflectance force from the sensor when the surgical instrument is placed near body tissue;
a modulator for modulating the reflectance force components in the controller robot; and
a motor for outputting through the controller robot a modulated reflectance force on the handle.

23. A surgical robot comprising:
a controller robot located between a handle and a surgical instrument;
a first sensor for sensing incident tremor force components (TF) present on the handle generated by the surgeon's hand;
a second sensor for sensing an incident motion force (MF) component present on the handle generated by the surgeon's hand natural motion (NM) as the surgeon moves the handle;
a first modulator for modulating and scaling the incident tremor force (MTF) components in the controller robot;
a second modulator for modulating and scaling the incident motion force (MMF) components in the controller robot;
a third modulator for creating a modulated and scaled output movement (MSOM) including the modulated and scaled incident motion force (MMF) and the modulated and scaled incident tremor force (MTF) in the controller robot for moving the surgical instrument via the controller robot, with all anatomically possible degrees of human hand motion freedom, in response to the natural movement (NM) inputted by the surgeon on the handle;
an first interface for outputting the modulated and scaled movement (MSOM) to move the surgical instrument with all anatomically possible degrees of human hand motion freedom, in response to a respective natural movement (NM) inputted by the surgeon on the handle;
a third sensor for sensing incident reflectance force (RF) components from the surgical instrument in the controller robot when the surgical instrument is near body tissue;
a fourth modulator for modulating and scaling the reflectance force (RFMS) components in the controller robot;
a second interface for outputting at the handle the modulated and scaled reflectance force (RFMS);
sensing contact in a binary manner with the tissue (TC) in the controller robot; and
a third interface for sending a contact signal to a display and creating in the controller robot a scaled jerk motion in the handle to represent contact to the surgeon.

* * * * *